Figure 1:
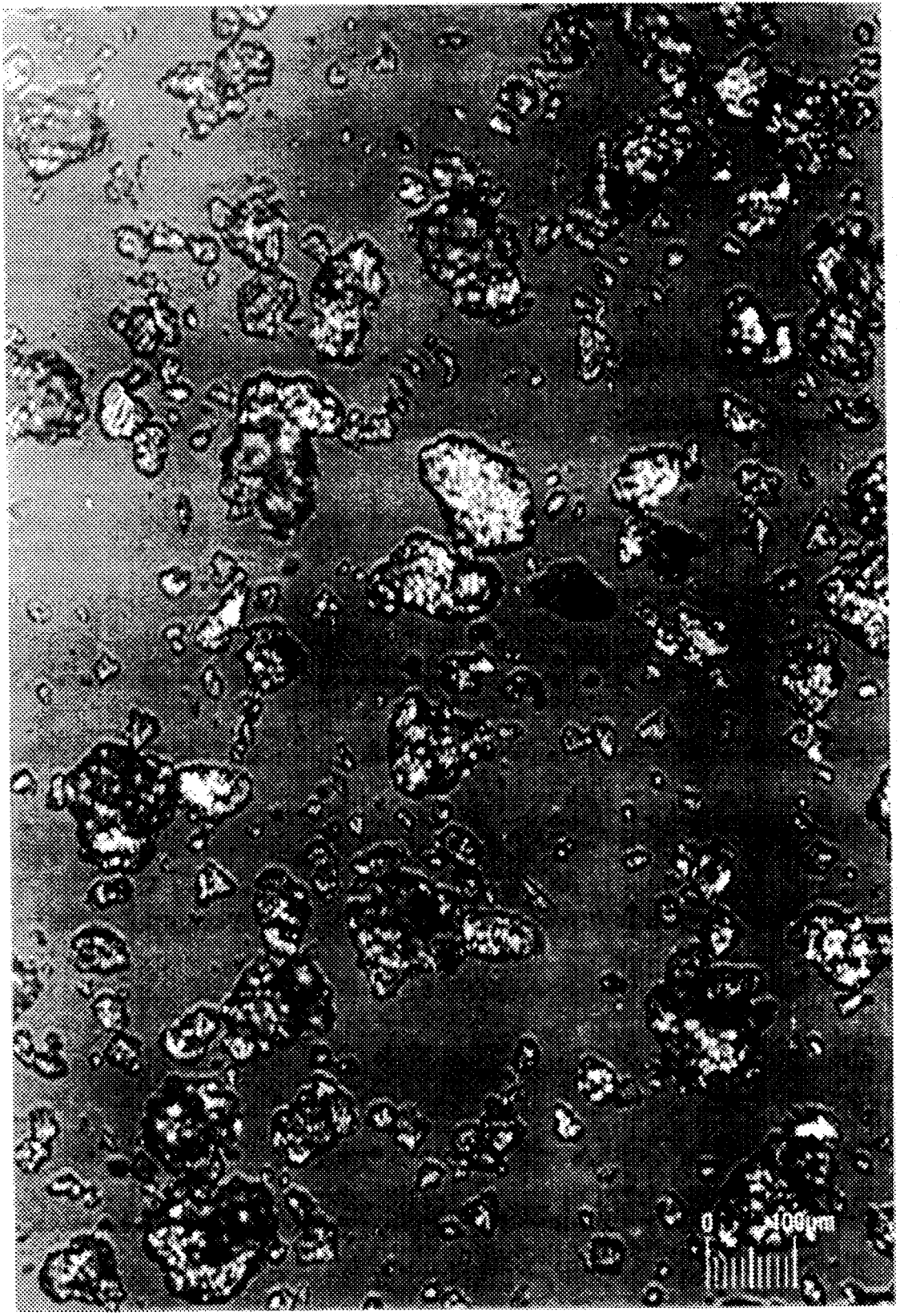

United States Patent [19]

Caboche

[11] Patent Number: 5,651,829
[45] Date of Patent: Jul. 29, 1997

[54] MALTITOL COMPOSITION AND PROCESS FOR PREPARING IT

[75] Inventor: Jean-Jacques Caboche, Bethune, France

[73] Assignee: Roquette Freres, Lestrem, France

[21] Appl. No.: 470,461

[22] Filed: Jun. 6, 1995

[30] Foreign Application Priority Data

Mar. 29, 1995 [FR] France .................................. 95 03732

[51] Int. Cl.$^6$ .......................... C08B 30/01; C08B 30/12; A23J 1/00; A61K 47/00
[52] U.S. Cl. ............................ 127/32; 127/29; 127/30; 127/40; 127/42; 536/1.11; 424/431; 426/656; 426/658
[58] Field of Search ................... 127/29, 30, 42, 127/40, 32; 536/1.11; 424/439; 426/656, 658

[56] References Cited

U.S. PATENT DOCUMENTS

| | | | |
|---|---|---|---|
| 3,915,736 | 10/1975 | Oyamada et al. | 127/29 |
| 3,918,986 | 11/1975 | Hiraiwa | 127/29 |
| 4,248,895 | 2/1981 | Stroz et al. | 426/3 |
| 4,408,041 | 10/1983 | Hirao et al. | 536/4.1 |
| 4,725,387 | 2/1988 | Hirao et al. | 264/6 |
| 4,831,129 | 5/1989 | Serpelloni | 536/124 |
| 4,846,139 | 7/1989 | Devos et al. | 127/40 |
| 5,354,856 | 10/1994 | Kawashima et al. | 536/127 |

FOREIGN PATENT DOCUMENTS

| | | |
|---|---|---|
| 48-61665 | 8/1973 | Japan . |
| 49-87619 | 8/1974 | Japan . |
| 49-110620 | 10/1974 | Japan . |
| 57-47680 | 4/1975 | Japan . |
| 50-59312 | 5/1975 | Japan . |
| 50129769 | 10/1975 | Japan . |
| 51-113813 | 10/1976 | Japan . |
| 58-158145 | 9/1983 | Japan . |
| 1383724 | 2/1975 | United Kingdom ......... C07D 309/10 |

OTHER PUBLICATIONS

"X-ray cristal structure of maltitol" Shoichi Ohno et al. Carboydrate Research 108– (1982) 163–171 Jan. 1982.

*Primary Examiner*—Asok Pal
*Assistant Examiner*—Patricia L. Hailey
*Attorney, Agent, or Firm*—Larson & Taylor

[57] ABSTRACT

The invention relates to a novel crystalline maltitol composition which essentially exhibits a porous and honeycombed structure and which possesses a very high degree of maltitol purity and a low density.

This composition possesses outstanding functional properties, making its use particularly recommended for manufacturing tablets or various powders to be dissolved in water.

The invention also relates to a novel process for enabling the crystalline maltitol composition to be manufactured.

22 Claims, 6 Drawing Sheets

MALTITOL COMPOSITION AND PROCESS FOR PREPARING IT

The present invention relates to a novel crystalline maltitol composition which is of very high purity and of low density. The invention also relates to a specific process for obtaining this composition and to uses of the latter in industry.

4-O-alpha-D-Glucopyranosyl-D-glucitol, commonly termed maltitol, is a polyol which is obtained industrially by hydrogenating maltose. It is of great interest due to the fact that it is more stable chemically and less calorific than sucrose, while advantageously possessing organoleptic properties which are very akin to those of this sugar. Furthermore, maltitol possesses the particular feature of not being cariogenic, something which opens up to it, and has already opened up to it, a multiplicity of applications in industry, particularly in the foodstuff and pharmaceutical industries.

For a very long time, maltitol was only available in the form of low-concentration syrups. For example, this polyol is the main compound present in the syrups LYCASIN® 80/55 and MALTISORB® 75/75, which have been marketed for almost twenty years by the Applicant. The maltitol contents in these syrups never exceed 75% of their dry matter.

After that, maltitol was marketed in the form of amorphous and impure powders. Thus, solutions of maltitol were often dried by atomization. It can be seen from the literature that this technique has always been considered to be particularly difficult to implement due both to a substantial degree of adhesion in the spray towers and the very hygroscopic nature of the powders thus obtained. Numerous patents bear witness to the substantial amount of work which has been directed towards remedying these problems. Examples which may be cited are:

Patents GB 1 383 724, JP 49-87619 and U.S. Pat. No. 4,248,895, which propose adding a variety of substances, such as alginates, celluloses, modified starches, polyvinylpyrrolidone, hydrophilic polymers, proteins or proteinaceous extracts, to the maltitol solutions prior to atomization with a view to reducing adhesion in the atomizing towers;

Patents JP 50-59312 and JP 51-113813, which describe methods for atomizing anhydrous compositions of molten maltitol;

Patents JP 49-110620, U.S. Pat. Nos. 3,918,986, 3,915,736, JP 50-129769 and JP 48-61665, which give methods which are directed towards reducing the hygroscopicity of the anhydrous maltitol powders either by adding anti-clumping substances or by enveloping the maltitol powders with saccharides, polyols or fatty substances, or by wet granulation.

It was only around 1980 that success was achieved for the first time in producing maltitol crystals. Previously, this polyol had always been considered to be a noncrystallizable product. This erroneous postulate, which was firmly anchored in peoples' minds for a long time, in reality originates from the fact that crystallization of maltitol from a supersaturated solution is not as spontaneous as it is in the case of other polyols such as mannitol, erythritol or isomalt, for example. Certain characteristics which are peculiar to maltitol, such as, in particular, its viscosity and its solubility, are likely to be at the root of the difficulties which have been noted.

The only crystalline form of maltitol which is presently known is the anhydrous form, which is described in U.S. Pat. No. 4,408,041 from the HAYASHIBARA company. For information on the characteristics of this crystalline form, reference may be made, if necessary, to this patent, which was filed in 1981, or to the article "X-ray crystal structure of maltitol (4-O-alpha-D-glucopyranosyl-D-glucitol)" by SHOICHI OHNO et al., which appeared in Carbohydrate Research, 108(1982), 163–171. Some years later, the first pseudo-crystalline powders of maltitol appeared on the market. These were, and certain of them still are, prepared by a technique termed "solidified" technique, which consists in solidifying a dehydrated solution of maltitol, having a concentration which can reach at best 90%, by adding a seed consisting of crystals of sugars or of polyols. Such a process is described, for example, in the documents JP 57-47680 and JP 58-158145.

U.S. Pat. No. 4,408,401, cited above, has also proposed preparing pulverulent crystalline mixtures, termed "total sugar", by atomizing pre-crystallized solutions or "massescuites". These are obtained by very slowly cooling a supersaturated aqueous solution of maltitol which also contains large quantities of other polyols such as sorbitol, maltotriitol and maltotetraitol, and other polyols having a higher degree of polymerization.

This very slow cooling, and the addition of a crystalline maltitol seed, causes maltitol crystals to appear and grow in the solution. When from 25 to 60% of the maltitol of this aqueous solution has crystallized, atomization is then carried out at a very low temperature, that is as indicated, at a temperature of between 60 and 100° C., in order not to cause the crystals which have been deliberately generated to disappear. As a result of this, the "total sugar" obtained contains from 25 to 60% of maltitol which is crystallized in the form of crystals which are completely identical to those obtained by means of crystallizing in water. The disadvantages arising from the presence of such crystals for certain specific applications will be seen below.

Moreover, this "total sugar" is far from being sufficiently crystalline, since it is indicated, if reference is made to the description, in particular to Example 4, that it requires both to be dried further, for approximately 40 minutes, and also to be aged for 10 hours. It can be seen that this process, which is very time-consuming, does not appear ever to have been the subject of any development or to be of the slightest interest.

A decisive step in developing crystalline powders of maltitol of very high concentration was taken, thanks to the work of the Applicant, by developing novel manufacturing processes which were based on the use of techniques for fractionating by means of continuous chromatography. These processes, which are the subject-matter of Patents EP 0 185 595 and EP 0 189 704, render it possible to obtain, at a competitive cost, powders having a purity reaching 99% simply by means of crystallizing in water the maltitol which is present in a chromatographic fraction which is particularly rich in this polyol. A crystalline powder of this nature has, for example, been marketed for several years now by the Applicant under the designation crystallized MALTISORB®.

The so-called "solidified" technique on the one hand, and the technique of crystallization in water on the other hand, are nowadays almost the only processes which are employed industrially. The products thus obtained, whose crystallinity is very variable, are particularly well suited to certain applications such as those of chewing gum and chocolate.

On the other hand, there are other applications for which these products are not completely satisfactory. This is the case, for example, when it is desired to use maltitol for replacing sucrose or lactose in dry pharmaceutical forms such as capsules, medicaments of the dissolving powder type, tablets and pulverulent nutrient preparations for dilution. This is also the case when it is desired to carry out the same type of substitution in sweetened foods such as powdered drinks, desserts, preparations for cakes, or chocolate-flavoured or vanilla-flavoured powders for breakfast.

It may be noted that, for these particular applications, both the psuedo-crystalline powders of maltitol, obtained by the "solidified" technique, and the crystalline powders of maltitol which contain crystals obtained by crystallization of maltitol in water, exhibit one or more drawbacks such as, in particular, those of flowing with difficulty, of being subject to solidification or clumping, of only dissolving very slowly in water, of being poor excipients for compression, or of not meeting the identification and purity criteria imposed by different pharmacopoeias.

It has, nevertheless, already been proposed, in the case of multitol, to use extrusion to improve its suitability for compression. Such a method is described, for example, in European Patent 0 220 103, of which the Applicant is the proprietor. This method is not ideal due to the fact that it, unfortunately, does not allow improvement in all the above-noted drawbacks of the products on the market.

Wishing to improve the state of the art, the Applicant has therefore attempted to develop a maltitol composition which does not have the drawbacks as regards flow, clumping, dissolution or compression which the known maltitol powders exhibit. Of course, it might have been thought that the identified need could be satisfied by other polyols. However, it is found that this is not at all the case since none of the other polyols possesses characteristics of solubility, hygroscopicity, sweet flavour and melting which are as close to those of sucrose as are those of maltitol.

It is the merit of the Applicant to have succeeded, against all expectations and after having carried out in-depth research on the subject, in preparing a crystalline maltitol composition which does not exhibit the mentioned defects of the known maltitol powders. The Applicant has demonstrated that, surprisingly and unexpectedly, it was possible to prepare such a crystalline composition under specific conditions, starting with a syrup having a maltitol concentration greater than 92%, by means of a process which is similar to atomization, although it was never possible in the past to use this technique to obtain maltitol crystallization directly. Furthermore, it should be noted that the atomization technique had fallen totally into abeyance as far as maltitol was concerned, once the possibility had been demonstrated of crystallizing this polyol from a supersaturated solution and following the advent of processes based on this principle and judged to be very effective.

The invention consequently relates, in the first place, to a crystalline maltitol composition which essentially exhibits a porous and honeycomb structure, a maltitol concentration which is greater than or equal to 92%, and an apparent density of between 100 and 700 g/l.

The concept of concentration is to be understood, in the case of the present invention, as corresponding to the percentage of maltitol expressed in dry weight in relation to the dry weight of the totality of carbohydrates present in the crystalline maltitol composition. These carbohydrates can be sugars such as, in particular, D-glucose, maltose, maltotriose and maltotetraose, and polyols derived by hydrogenating these sugars. As a rule, this concentration is measured by high performance liquid chromatography.

The first essential feature of the maltitol composition stems from the fact that it is crystallized, which confers on it a very high degree of stability with respect to humidity. Consequently, the tendency of the composition to solidify or clump is low. Thus, the composition is easy to use and it is not imperative to take draconian precautions to avoid such a risk.

The crystallinity of the composition according to the invention can be measured by means of differential thermal calorimetry. The latter is directly proportional to its heat of fusion, which is preferably greater than 130 J/g, more preferably greater than 145 J/g and still more preferably greater than 155 J/g.

It has been found in a surprising and unexpected manner that the composition according to the invention always has a crystallinity significantly higher than a maltitol "massé" or a solidified maltitol, a crystallinity generally higher than an extruded maltitol of equivalent richness in maltitol, and a crystallinity in general very slightly lower than a maltitol crystallized in water of equivalent richness in maltitol. It is thus that the composition according to the invention has an enthalpy of fusion comprised between 160 and 164 J/g whereas this enthalpy of fusion is ordinarily comprised between 80 and 120 J/g for a maltitol "massé" or solidified maltitol such as for example in the case of the powder MALBIT®CR, is comprised between 130 and 145 J/g for an extruded maltitol and is comprised between 163 and 167 J/g for a maltitol crystallized in water such as the product crystallized MALTISORB®, manufactured and sold by the applicant.

It has also been noted that a composition according to the invention presents a melting temperature comprised between 148 and 150° C., generally around 149° C. This temperature tends to be slightly weaker than that of a maltitol crystallized in water of equivalent richness in maltitol.

According to a second essential feature, the crystalline maltitol composition according to the invention possesses a maltitol concentration which is at least equal to 92%. Preference is given, so that the composition can crystallize immediately and more completely, to a composition which exhibits a maltitol concentration which is greater than or equal to 95%, and, better still, greater than or equal to 98%. The ideal is to achieve a concentration which is in the vicinity of, or greater than, 99%.

Furthermore, it is also preferred that the composition according to the invention only contains a low content of polyols other than maltitol, it being possible, in particular, for these polyols to be sorbitol, xylitol, mannitol, iditol, arabitol, maltotriitol or maltotetraitol. The content of these polyols is preferably less than 5% and, better still, less than 2% in relation to the dry matter of the composition. Thus, it has been observed that their presence significantly impairs the crystallinity of the composition according to the invention. This is not the case, or is much less the case, when the composition contains certain other substances. This explains why the crystalline maltitol composition can contain, without disadvantage, such substances in quite large quantity, depending on the use which is intended for it.

Examples of those substances which can be included, without any major problem, in the crystalline maltitol composition and which may be cited are intense sweeteners, colorants, perfumes, fragrances, vitamins, minerals, pharmaceutical or veterinary active principles, fatty acid esters, organic or inorganic acids and their salts, proteinaceous substances such as proteins, amino acids and enzymes.

According to a third essential feature, the crystalline maltitol composition according to the invention usually exhibits a density which is lower than those of known maltitol powders. This density can, for example, be measured using an apparatus marketed by the HOSOKAWA Company under the trade-name "Powder Tester" and applying the recommended method for measuring apparent density. Under these conditions, the composition according to the invention exhibits an apparent density of between approximately 100 and approximately 700 g/l, preferably of between 200 and 670 g/l and, more preferably, of between 300 and 650 g/l. Ordinarily, its apparent density is between 400 and 650 g/l.

The low density of the composition according to the invention is due to its special structure, which distinguishes it clearly from the known maltitol powders. Thus, it can be seen, by microscopic observation, that its structure is essentially porous and honeycombed. Furthermore, the particles making up the composition according to the invention are essentially spherical, lacking sharp edges and composed of a vast number of crystalline microparticles which are agglomerated to each other. This structure differs distinctly from that of a maltitol crystallized in water and that of an extruded maltitol, which consist of very angular cubic or parallele-pipedal particles, or of a solidified maltitol, which has a very dense structure comprising particles which are weakly birefringent in polarized light.

In this way, therefore, the crystalline maltitol composition according to the invention contains very few particles having shape and appearance characteristics which are similar to those found in the maltitol powders which are crystallized in water, extruded or solidified.

The crystalline composition according to the invention has in general a specific surface lower than 0.2 $m^2/g$.

Furthermore, the applicant has found, in measuring the porosity to mercury of particles between 160 and 250 microns, that, contrary to a maltitol powder crystallized in water, the composition according to the invention is constituted of particles possessing open pores of size comprised between 1 and 10 microns. The volume of these pores represent in general 0.01 to 0.03 $cm^3/g$, which value is lower than the ordinary volumes for a maltitol "massé" or solidified maltitol, or extruded powders.

The water content, determined by heating in an oven at 130° C. for 2 hours, of the crystalline maltitol composition according to the invention is preferably less than 2% and still more preferably less than 1%. In general, this content is even less than 0.5%, if not to say less than 0.35%.

As regards the functional characteristics of the crystalline maltitol composition according to the invention, the Applicant has evaluated its flowability using the apparatus marketed by the HOSOKAWA Company. This apparatus can be used to measure the flowability of a powder, under standardized and reproducible conditions, and to calculate a flow rating, which is also termed Carr index. The composition according to the invention has an excellent flow rating which is between 70 and 90. This value is preferably between 75 and 90 and still more preferably between 80 and 90. This value is very close to those of maltitol powders of the prior art which were obtained by extruding crystals which were crystallized in water.

Furthermore, the flowability of the composition according to the invention is usually markedly greater than those of maltitol powders which were obtained simply by crystallizing in water or by the "solidified" technique.

It is conceivable that the excellent flowability of the composition according to the invention can be explained by a combination of several of its physico-chemical characteristics, namely, in particular, the absence of substantial electrostatic charges on the surface of the particles of which it consists, its concentration of maltitol, its low hygroscopicity and, finally, the characteristic shape of the particles of which it consists. This excellent flowability is advantageous since it makes it very easy to fill and empty hoppers, receptacles or other containers such as, for example, sachets or capsules.

A second essential functional property of the crystalline maltitol composition according to the invention is that of dissolving very rapidly in water. In order to measure this speed of dissolution, a test A is carried out, which test consists of introducing 5 grams exactly of a granulometric 200 to 315 micron cut of the product to be tested into 150 grams of demineralized and degassed water which is maintained at 20° C. in a shallow 250 ml beaker and stirred at 200 rpm. The dissolution time corresponds to the time which is required, after having introduced the product, for the preparation to become perfectly clear visually. Under these conditions, the composition according to the invention generally exhibits a speed of dissolution which is less than 30 seconds, preferably less than 26 seconds and, still more preferably, less than 20 seconds. In general, these times are less than those obtained with any of the maltitol powders which are currently being marketed. Understandably, this ability to dissolve rapidly is an undeniable advantage, for example in manufacturing foodstuffs or pharmaceuticals which are to be dissolved before being ingested.

The crystalline maltitol composition according to the invention also possesses other advantageous characteristics. Those which may be cited are its very high degree of suitability for being compressed in order to prepare tablets for chewing or sucking and its very high degree of suitability for being mixed with other products.

The crystalline maltitol composition according to the invention can be obtained by atomizing a syrup, which is relatively rich in maltitol with respect to the quantity of carbohydrates present in this syrup, on a moving pulverulent bed of particles of crystallized maltitol of a purity which is at least equal to that of the syrup. It has been established that the maltitol concentration of the syrup should be greater than or equal to 92% to ensure that extensive crystallization of the maltitol can occur within a sufficiently short space of time.

In general, this maltitol syrup is a completely clear solution of maltitol or else a solution which is slightly opaque due to the possible, but undesirable, presence of fine crystals of maltitol.

The crystalline maltitol composition can, in particular, be obtained by implementing the process which comprises the following steps:

preparing a maltitol syrup which has a dry matter content of at least 50% and exhibits a maltitol concentration which is greater than or equal to 92%, finely atomizing this syrup on a moving pulverulent bed of particles of crystallized maltitol at a concentration which is at least equal to that of the syrup, with this bed having a temperature of between 60 and 110° C. and the mass of the bed consistently representing at least 2 times the mass of the atomized syrup, drying the pulverulent bed and the syrup in order to obtain the crystalline maltitol composition, where appropriate, maturing the crystalline maltitol composition until it exhibits a sufficient crystallinity and, preferably, a heat of fusion which is greater than or equal to 130 J/g, where appropriate, partially recycling the crystalline maltitol composition so that it constitutes a new pulverulent bed of crystallized maltitol.

Contrary to what might have been thought, this technique makes it possible to obtain a crystalline maltitol composition which is of low density and which dissolves rapidly in water. These properties can be adjusted by modifying the maltitol concentration of the syrup, the dry matter content of the syrup, the fineness of atomization, the nature of the particles of crystallized maltitol which form the pulverulent bed, the means by which these particles are moved, the temperature of the bed, the temperature of drying, and the respective masses of the bed and of the atomized syrup.

It is preferred that the maltitol concentration of the syrup should be greater than or equal to 95% and, better still, greater than or equal to 98%, with the ideal being to select a concentration which is close to or greater than 99%.

It is preferable to avoid coarse atomization of the syrup, which results in adhesion, poor crystallization of the maltitol and too great an increase in density, something which is not desired. Also, to ensure that the crystalline maltitol composition exhibits the specific properties described above, it is appropriate to choose equipment which enables very fine droplets, or even a mist, to be formed from the syrup.

As regards the nature of the particles of maltitol which constitute the pulverulent bed, it is preferred that these particles also exhibit a high maltitol concentration, in any case a concentration which is at least equal to that of the syrup employed. To obtain a good result, it is also preferable for this bed to be of rather low density as well, that is for this bed to have a density which is less than 700 g/l and, better still, less than 650 g/l. The ideal is to choose, for this bed, particles of maltitol exhibiting all the characteristics of the crystalline maltitol composition according to the invention. This can be achieved by partially recycling the composition according to the invention, which recycled composition then acts as the pulverulent bed of crystallized maltitol. It is very advantageous to proceed in this fashion, but it is then preferable to grind or sieve the composition according to the invention in order to retain only those particles having a size less than 150 microns and, better still, a size less than 90 microns.

The particles which constitute the pulverulent bed can be set in motion either mechanically or by blowing air. This latter possibility is preferred, since it is easy, by selecting the temperature of the air, to adjust the temperature of the bed to a value of between 60 and 110° C., and by regulating the air flows, to adjust the properties of the maltitol crystalline composition.

In general, it is preferred that the temperature of this bed should be maintained at between 65 and 90° C., with the ideal being to achieve a temperature which lies between 70 and 85° C. It is also preferred that the mass of the pulverulent bed should consistently be 3 times or, better still, 5 times the mass of the atomized syrup. When the composition according to the invention is partially recycled so that it can act as the pulverulent bed, it is sufficient to adjust the rate of entry of syrup so that it represents at most 25%, or, better still, at most 17%, of the rate of entry of recycled composition.

The drying of the pulverulent bed on which the syrup has been atomized should be carried out so as to obtain a final water content which does not exceed 2%, preferably 1%, and, more preferably, 0.5% of the composition.

The Applicant has demonstrated that it was possible advantageously to manufacture the crystalline maltitol composition continuously using, for example, an atomization tower of the M.S.D. type from the NIRO-ATOMIZER Company, which tower, thanks to its design, makes it possible to reproduce all the essential steps of the process according to the invention.

Thus, this apparatus renders it possible, by means of the nozzle which it contains, to very finely atomize a syrup having a temperature of between 50 and 100° C. and a dry matter content of between 55 and 85% on a bed of maltitol particles which is set and maintained in motion using air. Furthermore, this apparatus also allows simultaneous drying by means of hot air. It is advantageously possible to select an air entry temperature of between 160 and 300° C. and flow rates of entering substances such that the temperature of the air leaving the tower is between 60 and 130° C. and, still better, between 70 and 90° C. This apparatus also allows, where appropriate, the crystalline maltitol composition to be partially recycled and to be dispersed very finely at the top of the tower, around the nozzle for atomizing the syrup.

Subsequently, the crystalline maltitol composition which is obtained by the process according to the invention can, if necessary, be granulated so as to modify its particle size. This granulation can be effected in water, in steam, or using a syrup which preferably contains maltitol.

The crystalline maltitol composition according to the invention may advantageously be employed as a sweetening agent, filling agent or texturing agent, as an excipient or as a support for various additives. It is particularly recommended, by reason of its specific properties, for manufacturing tablets and powders for dissolving in the foodstuff and pharmaceutical spheres. Nevertheless, there is nothing to prevent its use for any other purpose as, for example, for formulating chewing gums, syrups or confectionery.

The invention will be understood still better with the aid of the following example, which is not intended to be limiting and simply instances certain embodiments and certain advantageous properties of the crystalline maltitol composition according to the invention.

EXAMPLE 1

Preparation of crystalline maltitol compositions of according to the invention, and comparison with products of the prior art.

A maltitol solution with a dry matter content of 75% is prepared by dissolving maltitol crystals having a maltitol concentration of 99.8%. This solution is brought to 80° C. and then maintained at this temperature.

This solution is atomized using a tower of the M.S.D. type from the NIRO ATOMIZER Company. In order to do this, approximately 100 kg of a powder of maltitol which has been crystallized in water, of fine particle size, is first introduced into the tower. The crystalline MALTISORB® P 90 powder, which is marketed by the Applicant, is used for this purpose. This powder acts as the pulverulent bed of crystallized maltitol. It is set in motion by being fluidized with air at 40°–90° C. and by being recycled at the top of the tower after having passed through a pulverizer which produces particles of crystallized maltitol having a size less than 90 microns.

The syrup is then finely atomized on the pulverulent bed of moving particles of crystallized maltitol by adjusting the flow rates of the substances entering the tower such that the quantity of this atomized syrup does not represent more than 25% of the recycled quantity of pulverulent maltitol. The temperature of the drying air at the upper tower inlet is selected to be between 165 and 225° C. The temperature of the air leaving the tower is between 70 and 90° C.

Under these conditions, it is observed that, after the tower has been in operation for 7 hours, the maltitol composition leaving the tower is virtually devoid of particles having shape and appearance characteristics similar to those found in the MALTISORB® P 90 powder. Thus, the composition is essentially porous and honeycombed and consists of particles which are essentially spherical, which lack sharp edges, and which are composed of a vast number of crystalline microparticles which are agglomerated with each other. This composition according to the invention is designated I1. Its principal characteristics are given in the table below.

The atomization of a solution of maltitol containing a lower concentration of maltitol is also effected exactly as indicated above. This solution contains 95.8% of maltitol and 2.9% of other polyols. After the tower has been in operation for 7 hours, it is observed that the departing product is well crystallized and exhibits all the characteristics of the crystalline maltitol composition according to the invention. This product is designated I2. It is noted that this composition I2 has, despite its rather low maltitol concentration, surprisingly crystallized in a relatively short period of time and in a sufficiently complete manner, without there having been any requirement for carrying out supplementary drying and ageing by blowing air for from one to twenty hours, as recommended in U.S. Pat. No. 4,408,041.

Compositions I1 and I2 according to the invention are compared with different maltitol powders of the prior art, that is:

a crystalline powder which contains maltitol crystals which are obtained by crystallization in water (MALTISORB® P 200);

a powder which is obtained by the so-called "solidified" technique (AMALTY® MR from the TOWA CHEMICAL Company);

and a maltitol powder which is extruded in accordance with the conditions given in Patent EP 0 220 103.

Figure 2:
Figure 3:
Figure 4:

The structures of the various products are observed in an optical microscope, in polarized light, and in an electron microscope using granulometric cuts of from 0 to 100 microns. Comparison of negatives which are obtained in the optical microscope and which correspond to composition I1 (FIG. 1), the MALTISORB® powder, which is crystallized in water (FIG. 2), the AMALTY® MR solidified powder (FIG. 3) and the extruded powder (FIG. 4) indicates:

that only the AMALTY® MR solidified powder fails to polarize light, thereby providing evidence of low crystallinity or of a high degree of crystalline disorder, that composition I1 according to the invention essentially consists of spherical particles without sharp edges, thereby distinguishing it very clearly from the powders which are crystallized in water and extruded.

Figure 5:
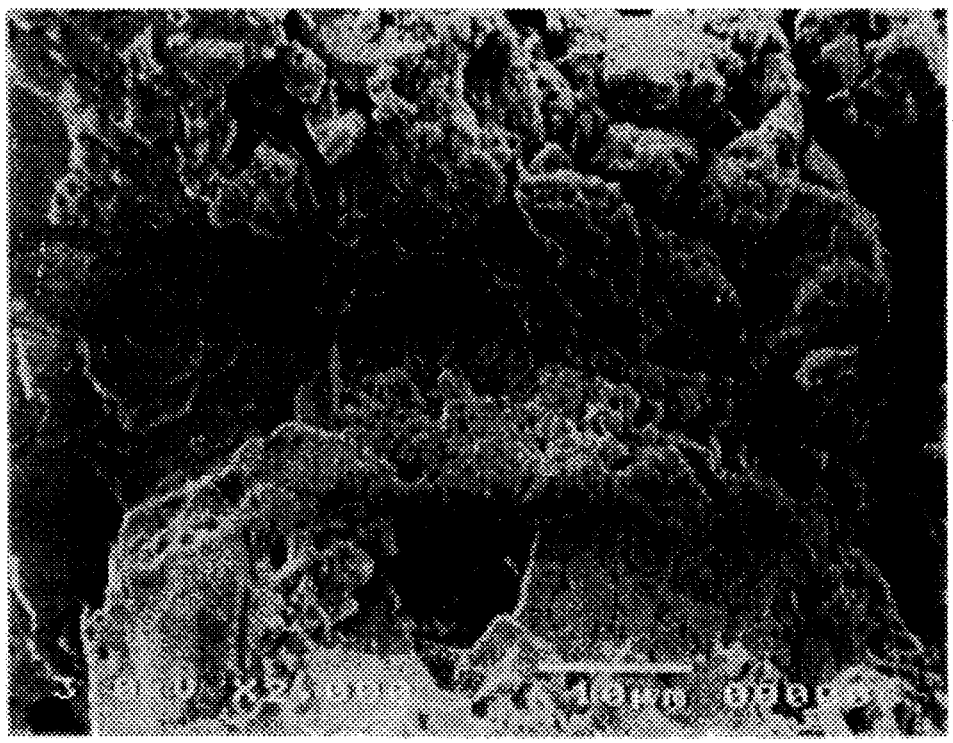
Figure 6:
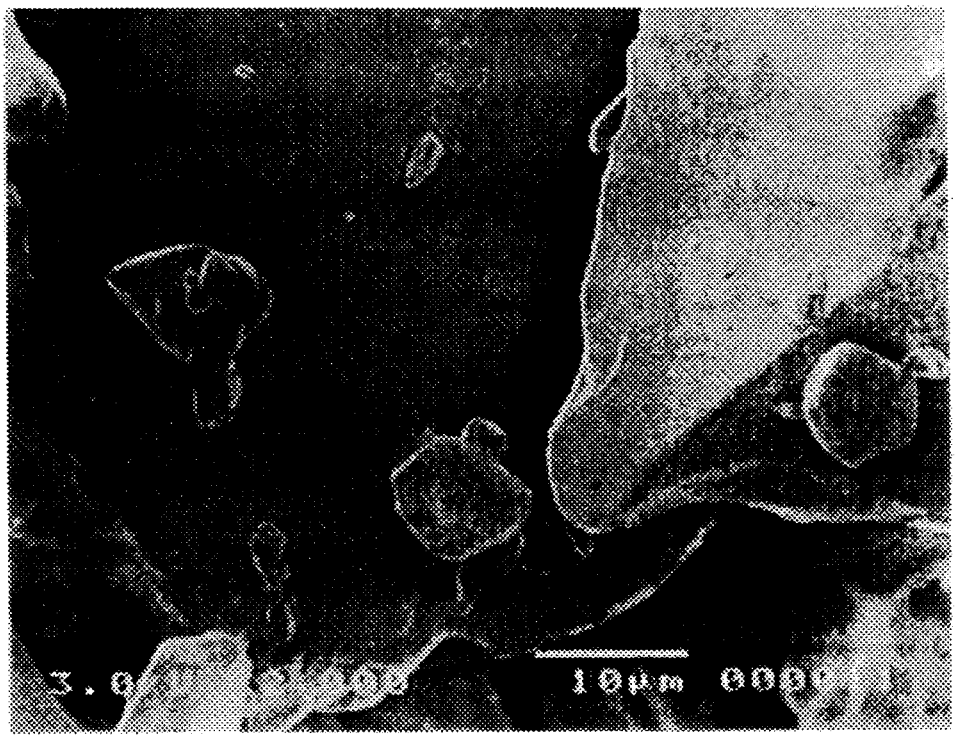
Figure 7:
Figure 8:
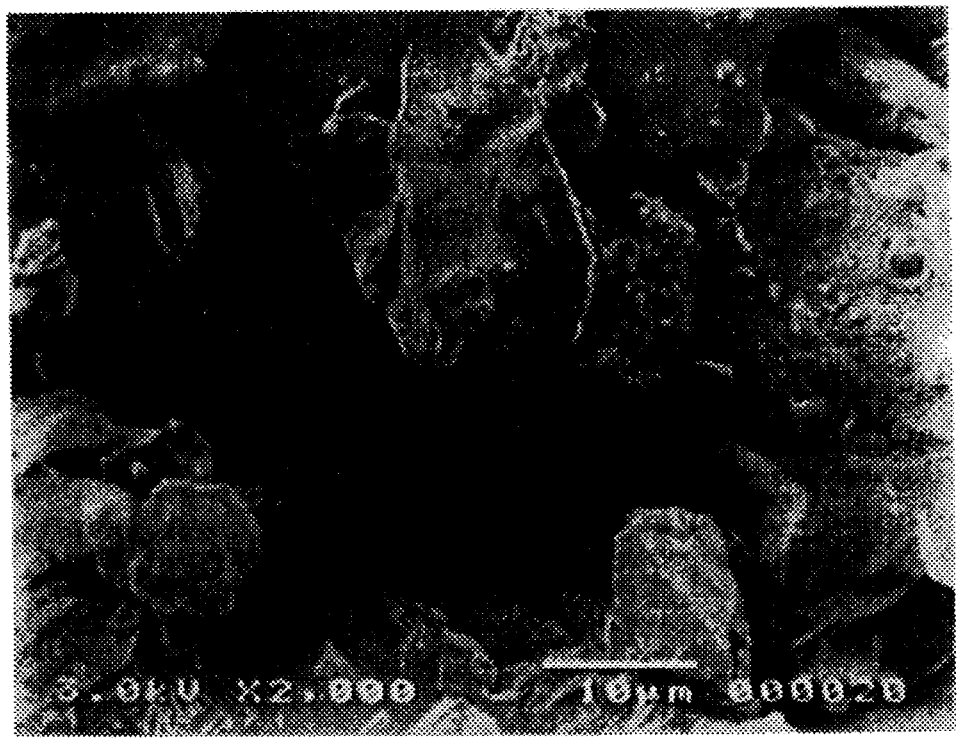

Comparison of the photographs, obtained by electron microscopy, for composition I1 (FIG. 5), the powder which is crystallized in water (FIG. 6), the solidified powder (FIG. 7) and the extruded powder (FIG. 8) demonstrates that the crystalline maltitol composition according to the invention essentially possesses a porous and honeycombed structure and contains particles which are composed of crystalline microparticles which are agglomerated with each other. The density of these particles appears to be markedly lower than that of the particles of the products of the prior art. Thus, these latter particles exhibit a dense and compact structure, with smooth or prickly particle surfaces which are very different from those found in the composition according to the invention.

Several functional characteristics of compositions I1 and I2 according to the invention are given in the following table. Contrary to the compositions of the prior art, the compositions according to the invention advantageously combine properties which have hitherto never been found at one and the same time. Thus, they possess, at one and the same time, the characteristics of being compressible, of flowing readily, and of dissolving very rapidly in water.

Furthermore, it appears that they are very weakly hygroscopic, which is an undeniable advantage when they are stored and used.

TABLE

| | Compositions according to the invention | | Compositions of the prior art | | |
|---|---|---|---|---|---|
| | | | Crystallized in water | Solidified | Extruded |
| | I1 | I2 | | | |
| Maltitol concentration | 99.8% | 95.8% | 99.8% | 92.0% | 98.0% |
| Water content (oven heating) | 0.3% | 0.7% | 0.2% | 0.8% | 0.2% |
| Content of polyols other than maltitol | traces | 2.9% | traces | 7.5% | 0.5% |
| Heat of fusion (±2 J/g) | 162 J/g | 134 J/g | 163 J/g | 120 J/g | 176 J/g |
| Peak melting temperature (±0.5° C.) | 149° C. | 146° C. | 149° C. | 144° C. | 149° C. |
| Structure | porous and honeycombed agglomerated microcrystals | | nonporous, very dense | relatively dense and compact | nonporous and dense |
| Density | 645 g/l | 639 g/l | 860 g/l | 720 g/l | 783 g/l |
| Carr flow index | 83.0 | 82.5 | 78.0 | 78.0 | 79.0 |
| Speed of dissolution (Test A) | 25 s | — | 68 s | 15 s | 34 s |
| Compressibility (Test from Patent EP 0 220 103) | 135 N | 68 N | impossible to measure | impossible to compress in this state | 140 N |

EXAMPLE 2

Comparison between compositions according to the invention and products of the prior art obtained according to the U.S. Pat. No. 4,408,401

"Total sugar" are prepared according to the prior art by simple atomization of pre-crystallized solutions of a "massecuite" of maltitol.

For this, the recommendations given in the U.S. Pat. No. 4,408,401 are followed, in using crystalline suspensions of 98% richness in maltitol, containing about 25 to 60% of maltitol crystals.

The characteristics of "total sugar" thus obtained are compared to those of compositions I.1 and I.2 of example 1 according to the invention.

It is noted that the "total sugar" present a dense structure and apparent density always greater than 700 g/l the other characteristics also being very close to a product crystallized in water. Thus, the speed of dissolution in water of these "total sugar" are close to 70 seconds and with these products it is not possible to manufacture tablets according to the test disclosed in European patent EP 0 220 103, even when increasing the tableting strengths.

It is observed that the "total sugar" of the prior art do not exhibit the advantageous physical and functional characteristics of composition I.1 and I.2 in accordance with the invention.

EXAMPLE 3

Sugarless chewing-gums are prepared according to the following formulation:

| | |
|---|---|
| gum | 247 g |
| maltitol powder | 543 g |
| LYCASIN® 80/55 maltitol syrup | 198 g |
| Spearmint flavour | 12 g |

Are used, as maltitol powders:
- a particle size cut of from 200 to 315 microns prepared from composition I.1 according to the invention and disclosed in example 1,
- and a particle size cut of from 200 to 315 microns, obtained from a MALTISORB®P200 water-crystallized maltitol powder.

A comparison is made between the textures of the sugar-free chewing-gums obtained in strictly identical conditions using the maltitol powders disclosed hereabove.

On taste testing, it is noticed that, although the powders which are used are particularly coarse, the cut according to the invention imparts to the chewing-gum a smoother and definitely less sandy texture than the cut of water crystallized maltitol.

It is also observed that the hardness of the chewing-gum samples containing the cut according to the invention is advantageously greater than the hardness of the samples prepared with the cut according to the prior art. This is confirmed by a hardness measurement by penetrometry with an INSTRON® device.

This comparison confirms the interest of the composition according to the invention when one is willing to adjust the texture in a chewing-gum formulation.

The crystalline composition according to the invention can also be used without any inconvenience for chewing-gum coating, by using it either in powder form or in syrup form.

I claim:

1. Crystalline maltitol composition having essentially a porous and honeycombed structure, a maltitol concentration which is greater than or equal to 92%, and an apparent density of between 100 and 700 g/l.

2. Composition according to claim 1, wherein the maltitol concentration is greater than or equal to 95%.

3. Composition according to claim 2, wherein the maltitol concentration is greater than or equal to 98%.

4. Composition according to claim 3, wherein the maltitol concentration is greater than or equal to 99%.

5. Composition according to claim 1, exhibiting a heat of fusion higher than 130 J/g.

6. Composition according to claim 5, wherein the heat of fusion is higher than 145 J/g.

7. Composition according to claim 6, wherein the heat of fusion is higher than 155 J/g.

8. Composition according to claim 1, containing in weight of dry matter, less than 5% of polyols other than maltitol.

9. Composition according to claim 1, containing in weight of dry matter, less than 2% of polyols other than maltitol.

10. Composition according to claim 1, exhibiting an apparent density of between 200 and 670 g/l.

11. Composition according to claim 10, exhibiting an apparent density of between 300 and 650 g/l.

12. Composition according to claim 11, exhibiting an apparent density of between 400 and 650 g/l.

13. Composition according to claim 1, exhibiting a Carr flow rating of between 70 and 90.

14. Composition according to claim 13, exhibiting a Carr flow rating of between 75 and 90.

15. Composition according to claim 14, exhibiting a Carr flow rating of between 80 and 90.

16. Composition according to claim 1, exhibiting a water content which is less than 2%.

17. Composition according to claim 16, exhibiting a water content which is less than 1%.

18. Composition according to claim 17, exhibiting a water content which is less than 0.5%.

19. Composition according to claim 1, containing one or more additives which are selected from the group consisting of intense sweeteners, colorants, perfumes, fragrances, vitamins, minerals, pharmaceutical or veterinary active principles, fatty esters of fatty acids, organic and inorganic acids and their salts, proteinaceous substances such as proteins, amino acids and enzymes.

20. Composition according to claim 1, exhibiting a speed of dissolution in water, according to a test A, which is less than 30 seconds.

21. Composition according to claim 20, exhibiting a speed of dissolution in water, according to a test A, which is less than 26 seconds.

22. Composition according to claim 21, exhibiting a speed of dissolution in water, according to a test A, which is less than 20 seconds.

* * * * *